(12) United States Patent
West

(10) Patent No.: US 10,002,190 B2
(45) Date of Patent: Jun. 19, 2018

(54) MEDICAL TREATMENT DEVICE WITH SPEAKER SOUND DETECTION

(71) Applicant: GAMBRO LUNDIA AB, Lund (SE)

(72) Inventor: William Joseph West, Plymouth, MN (US)

(73) Assignee: Gambro Lundia AB, Lund (SE)

( * ) Notice: Subject to any disclaimer, the term of this patent is extended or adjusted under 35 U.S.C. 154(b) by 0 days. days.

(21) Appl. No.: 15/554,065

(22) PCT Filed: Apr. 1, 2016

(86) PCT No.: PCT/US2016/025572
§ 371 (c)(1),
(2) Date: Aug. 28, 2017

(87) PCT Pub. No.: WO2016/164268
PCT Pub. Date: Oct. 13, 2016

(65) Prior Publication Data
US 2018/0075203 A1  Mar. 15, 2018

Related U.S. Application Data

(60) Provisional application No. 62/143,385, filed on Apr. 6, 2015.

(51) Int. Cl.
*G08B 21/00* (2006.01)
*G06F 17/30* (2006.01)
(Continued)

(52) U.S. Cl.
CPC ........ *G06F 17/30743* (2013.01); *G06F 3/162* (2013.01); *H04R 29/001* (2013.01)

(58) Field of Classification Search
CPC ........... G06F 17/3074; G06F 17/30743; G06F 17/30749; G06F 17/30778; G06F 3/16;
(Continued)

(56) References Cited

U.S. PATENT DOCUMENTS 5,736,927 A  4/1998  Stebbins
6,094,134 A  7/2000  Cohen
(Continued)

FOREIGN PATENT DOCUMENTS

WO  WO 2013/153484  10/2013
WO  WO 2015/062896  5/2015

OTHER PUBLICATIONS

PCT/US2016/025572 International Preliminary Report on Patentability dated Oct. 19, 2017 (12 pages).
(Continued)

*Primary Examiner* — Van Trieu
(74) *Attorney, Agent, or Firm* — Mueting, Raasch & Gebhardt, P.A.

(57) ABSTRACT

Medical treatment devices and methods may include a speaker operable to broadcast one or more types of sounds, wherein each type of sound may be associated with a predefined sound signature. An acoustic transducer may be used to generate a sound signal representative of a sound when broadcast by the speaker. The speaker may be commanded to broadcast a sound of the one or more types of sounds, a sound signal generated by the acoustic transducer during a time period when the speaker is expected to broadcast the sound may be monitored, and it may be determined if the speaker was operable to broadcast the sound and whether the sound was audible to a user by comparing the stored sound signal to the sound signature associated with the type of sound commanded to be broadcast.

17 Claims, 9 Drawing Sheets

(51) Int. Cl.
*H04R 29/00* (2006.01)
*G06F 3/16* (2006.01)

(58) Field of Classification Search
CPC .......... G06F 3/162; G06F 3/167; G06F 19/00;
H04R 29/00; H04R 29/001; H04R
29/007; H04R 29/008; G08B 21/00;
G08B 25/14
See application file for complete search history.

(56) References Cited

U.S. PATENT DOCUMENTS

| | | | |
|---|---|---|---|
| 7,911,353 B2 | 3/2011 | Bedingfield | |
| 7,995,732 B2* | 8/2011 | Koch | H04M 3/42221 |
| | | | 379/202.01 |
| 9,357,320 B2* | 5/2016 | Gelter | H04R 29/00 |
| 9,591,419 B2* | 3/2017 | Gelter | H04R 29/00 |
| 2007/0109115 A1 | 5/2007 | Kiani | |
| 2009/0295591 A1 | 12/2009 | Bedingfield | |
| 2012/0286946 A1 | 11/2012 | Karl | |
| 2015/0054651 A1 | 2/2015 | Halbert | |

OTHER PUBLICATIONS

PCT/US2016/025572 International Search Report and Written Opinion dated Jan. 8, 2016 (16 pages).

* cited by examiner

MEDICAL TREATMENT DEVICE WITH SPEAKER SOUND DETECTION

CROSS-REFERENCE

This application is a U.S. National Stage Application of International Application No. PCT/US2016/025572, filed Apr. 1, 2016 and published in English on Oct. 13, 2016 as International Publication No. WO 2016/164268 A1, which claims the benefit under 35 U.S.C. 119(e) of U.S. Provisional Application Ser. No. 62/143,385, filed on 6 Apr. 2015, which are all incorporated herein by reference in their entirety.

BACKGROUND

The disclosure herein relates to medical treatment devices and methods for treatment. More particularly, the disclosure relates to medical treatment devices and methods that use one or more speakers to broadcast sounds (e.g., alarms, test sounds, etc.) and, for example, test such speakers.

Medical treatment devices, such as extracorporeal blood treatment devices or systems, may provide any number of life-sustaining tasks (e.g., dialysis, oxygenation, etc.). Such medical treatment devices are not exempt from machine malfunction, and various problems may be experienced during performing the treatment. For example, if the medical treatment device experiences a malfunction or a therapy problem occurs, a user may be notified thereof upon detection, a backup or redundant process may be initiated upon detection, or one or more other processes may be performed to correct the situation.

For example, in one or more circumstances, one or more alarms may be provided to a user, such as visually with use of a warning light or an alarm notice on a display and/or an alarm sound. For example, various alarm sounds for various circumstances may be provided to a user upon detection of a malfunction. If for any reason the alarm sound does not sound or it cannot be heard, the user may need to rely on the visual alarm or alert to correct the alarm condition. For example, the alarm sound may not sound for various reasons (e.g., a speaker malfunction, a connectivity fault in the chain between controllers and/or drivers of the medical treatment device and the speaker, etc.).

Medical devices (e.g., devices providing medical therapies) typically include safety systems that perform, for example, power on self-tests or other on-going tests (e.g., after the device is power cycled, as part of ongoing system self-test to ensure the device operates safely, etc.). For example, one or more of such tests may include: supply voltage tests; clock accuracy tests, battery health checks; and system safety tests such as, one or more tests to determine proper functioning of device speakers.

In many cases, for example, such tests to determine proper functioning of alarms (e.g., speaker functionality, speaker connectivity functionality, speaker driver functionality, etc.) may require complicated algorithms that require a relatively large amount of additional processing time. For example, this may be the case when the frequency of the tones of a sounded alarm is used in such algorithms.

SUMMARY

In one or more embodiments of the present disclosure, devices and methods may provide independent confirmation that an alarm was broadcast and was audible to the user (e.g., the sound broadcast was loud enough to be heard). For example, this may be implemented by monitoring a microphone, analyzing the data resulting from such monitoring, and providing a detection state (e.g., with respect to whether the alarm was broadcast and was audible to a user).

Further, for example, although one or more alarms may be used and/or confirmed, one or more embodiments of devices and methods of the present disclosure may not check to determine which alarm was sounded, but only determine that an alarm sound was broadcast and was audible to a user. For example, at least in one embodiment, the determination of which alarm was sounded is not determined because a purpose of the algorithm is to determine if the alarm was audible to a user, not perform software verification testing of, e.g., source audio hard coded into the machine. However, at least in one embodiment, one or more the algorithm may be used to determine which alarm was sounded (e.g., use of note spacing to determine between such alarms).

However, for example, at least in one embodiment, frequency information of the sounds are not used to detect that an alarm sound was broadcast and was audible to a user. For example, such frequency of tones may not be used because it may add additional complication and processing that is not needed for accurate alarm detection and because much of the frequency content is lost and shifted from the source to the speaker, microphone, digital sampling, and acoustics within the machine and the ambient environment.

One or more embodiments of the present disclosure provides independent confirmation that an audible signal (e.g., a sound, such as an alarm or beep), was broadcast and was audible to a user. For example, such confirmation may be accomplished by analyzing the results of an audio recording captured during the expected audio signal broadcast.

At least in one or more embodiments, the analysis may, for example, be performed by an algorithm that processes the recording, filters the signal, and applies logic to detect the presence of a signal. Further, at least in one or more embodiments, the analysis may include one or more of the following features and/or processes: an algorithm portion may process the audio to match the range of the detector and compensate for the predefined recording environment; the audio signal may be filtered to extract information about any potential audio signals from the recording; a filter used may be a combination of a difference/amplitude filter and a first order low pass filter; a filter used may be a filter combination that is computationally easy and efficiently provides a signal to be used for detection; an algorithm portion that checks the filtered amplitude for specific audio detection criteria; criteria that may be used by the algorithm may be predetermined based on the expected amplitude, duration, and the number of audio signals in the recording; and/or an algorithm portion may provide an algorithm output of such logical conditions indicative of the presence of a specific audio signal in the recording. For example, such an output may be indicative of or proof that the audio sound was broadcast, audible to a user, and the speaker was in good working order.

One or more embodiments of the present disclosure provide a device and/or method that may facilitate an independent confirmation of a broadcast audio sound (e.g., prove that when an alarm is commanded to sound, it was commanded correctly, it was audible to a user, and the speaker was in good working order); that may provide criteria and detection conditions tunable to adapt to different audio signal characteristics or environmental conditions; that may provide an algorithm that is computationally simple and can be implemented with low-cost hardware and still return results quickly; and/or may provide an algorithm that is robust because it checks many characteristics of recording, including amplitude, duration, and number of audio signals present.

One exemplary embodiment of a medical treatment device for use in providing a treatment to a patient (e.g., that includes speaker sound confirmation functionality) includes a speaker operable to broadcast one or more types of sounds (e.g., the one or more types of sounds may include at least one of an alarm sound and a test sound; the alarm sound may include a plurality of spaced apart notes with each note having a duration, an amplitude, and a frequency; each test sound may include a note having a duration, an amplitude, and a frequency; etc.). Each type of sound may be associated with a predefined sound signature (e.g., the sound signature corresponding to an alarm sound may include criteria based at least on the amplitude and duration of at least two notes of the plurality of spaced apart notes, the sound signature corresponding to a test sound may include criteria based on the amplitude and duration of the note thereof). Further, the device may include an acoustic transducer to generate a sound signal representative of a sound when broadcast by the speaker and processing circuitry configured to command the speaker to broadcast a sound of the one or more types of sounds, monitor and store the sound signal generated by the acoustic transducer during a time period when the speaker is expected to broadcast the sound, and determine if the speaker was operable to broadcast the sound and whether the sound was audible to a user by comparing the stored sound signal to the sound signature associated with the type of sound commanded to be broadcast.

One exemplary embodiment of a method for a medical treatment device (e.g., that includes speaker sound confirmation functionality) may include providing a medical treatment device having a speaker operable to broadcast one or more types of sounds (e.g., wherein the one or more types of sounds may include at least one of an alarm sound and a test sound; each alarm sound may include a plurality of spaced apart notes with each note having a duration, an amplitude, and a frequency; each test sound may include a note having a duration, an amplitude, and a frequency; etc.). Further, the method may include commanding the speaker to produce a sound of the one or more types of sounds, wherein each type of sound is associated with a predefined sound signature (e.g., the sound signature corresponding to an alarm sound may include criteria based at least on the amplitude and duration of at least two notes of the plurality of spaced apart notes, the sound signature corresponding to a test sound may include criteria based on the amplitude and duration of the note thereof, etc.). Still further, the method may include monitoring and storing a sound signal generated by an acoustic transducer during a time period when the speaker is expected to broadcast the sound and determining if the speaker was operable to broadcast the sound and whether the sound was audible to a user by comparing the stored sound signal to the sound signature associated with the type of sound commanded to be broadcast.

Another exemplary embodiment of a medical treatment device for use in providing a treatment to a patient (e.g., that includes speaker sound confirmation functionality) may include a speaker operable to broadcast one or more types of sounds (e.g., the one or more types of sounds may include at least one of an alarm sound and a test sound; the alarm sound may include a plurality of spaced apart notes with each note having a duration, an amplitude, and a frequency; each test sound may include a note having a duration, an amplitude, and a frequency; etc.). Each type of sound may be associated with a predefined sound signature, wherein the sound signature corresponding to an alarm sound or a test sound is independent of frequency. The medical treatment device may further include an acoustic transducer to generate a sound signal representative of a sound when broadcast by the speaker and processing circuitry configured to command the speaker to broadcast a sound of the one or more types of sounds, monitor and store the sound signal generated by the acoustic transducer during a time period when the speaker is expected to broadcast the sound, and determine if the speaker was operable to broadcast the sound and whether the sound was audible to a user by comparing the stored sound signal to the sound signature (e.g., which is independent of frequency) associated with the type of sound commanded to be broadcast.

Yet another exemplary embodiment of a medical treatment device for use in providing a treatment to a patient (e.g., that includes speaker sound confirmation functionality) may include a speaker operable to broadcast one or more types of sounds, wherein the one or more types of sounds include a plurality of types of alarm sounds (e.g., each type of alarm sound may include a different plurality of spaced apart notes with each note having a duration, an amplitude, and a frequency) The plurality of types of alarm sounds may be associated with a common predefined sound signature, wherein the common predefined sound signature is based at least on the amplitude and duration of at least two notes of the plurality of spaced apart notes of each of the plurality of types of alarm sounds. The medical treatment device may further include an acoustic transducer to generate a sound signal representative of a sound when broadcast by the speaker and processing circuitry configured to command the speaker to broadcast an alarm sound of the plurality of types of alarm sounds, monitor and store the sound signal generated by the acoustic transducer during a time period when the speaker is expected to broadcast the alarm sound, and determine if the speaker was operable to broadcast the alarm sound and whether the alarm sound was audible to a user by comparing the stored sound signal to the common predefined sound signature associated with the plurality of types of alarm sounds.

In one or more of the exemplary systems and/or methods, the one or more types of sounds may include a plurality of types of alarm sounds (e.g., wherein each type of alarm sound may include a different plurality of spaced apart notes with each note having a duration, an amplitude, and a frequency). The plurality of types of alarm sounds may be associated with a common predefined sound signature (e.g., the common predefined sound signature may be based at least on the amplitude and duration of at least two notes of the plurality of spaced apart notes of each of the plurality of types of alarm sounds). In such a circumstance, for example, commanding the speaker to broadcast a sound of the one or more types of sounds may include commanding the speaker to broadcast an alarm sound of the plurality of types of alarm sounds, and further, determining if the speaker was operable to broadcast the sound and whether the sound was audible to a user may include determining if the speaker was operable to broadcast the alarm sound and whether the alarm sound was audible to a user by comparing the stored sound signal to the common predefined sound signature associated with the plurality of types of alarm sounds.

Further, in one or more of the exemplary systems and/or methods, the one or more types of sounds may include a plurality of types of alarm sounds, wherein each type of alarm sound may include a different plurality of spaced apart notes with each note having a duration, an amplitude, and a frequency. Each of the plurality of types of alarm sounds may be associated with a predefined sound signature, wherein the predefined sound signature is based at least on the amplitude and duration of at least two notes of the plurality of spaced apart notes of each of the plurality of types of alarm sounds and the spacing between the plurality of spaced apart notes. Further, for example, in such a circumstance, commanding the speaker to broadcast a sound of the one or more types of sounds may include commanding the speaker to broadcast an alarm sound of the plurality of types of alarm sounds, and further, determining if the speaker was operable to broadcast the sound and whether the sound was audible to a user may include determining if the speaker was operable to broadcast the alarm sound and whether the alarm sound was audible to a user by comparing the stored sound signal to the predefined sound signatures associated with the types of alarm sounds.

One or more of the embodiments of devices and/or methods described herein may include one or more of the following features and/or processes: the criteria of a sound signature corresponding to an alarm sound or a test sound may be independent of frequency; where the sound is a test sound, comparing the stored sound signal to the sound signature of the test sound may include filtering the sound signal generated by the acoustic transducer to provide a filtered sound signal and comparing the amplitude of the filtered sound signal to an amplitude threshold of the sound signature (e.g., a test sound may be detected if the amplitude of the filtered sound is greater than the amplitude threshold for a time exceeding a duration time threshold of the sound signature); where the sound is an alarm sound, comparing the stored sound signal to the sound signature of the alarm sound may include filtering the sound signal generated by the acoustic transducer to provide a filtered sound signal and comparing the amplitude of the filtered sound signal to an amplitude threshold of the sound signature (e.g., a note of the plurality of notes defining the alarm sound being detected if the amplitude of the filtered sound is greater than the amplitude threshold for a time exceeding a note duration time threshold of the sound signature, and an alarm sound is detected if the number of detected notes exceeds a predetermined number within an alarm duration time threshold of the sound signature); filtering the sound signal generated by the acoustic transducer may include applying an amplitude/difference filter to the sound signal and then smoothing the signal to provide the filtered sound signal; applying an amplitude/difference filter to the sound signal may include taking a derivative of the sound signal; commanding the speaker to broadcast a sound of the one or more types of sounds may include commanding the speaker to broadcast at least two different alarm sounds having different patterns of spaced apart notes (e.g., wherein it may be determined whether the speaker was operable to broadcast each of the at least two different alarm sounds); each alarm sound of the at least two different alarm sounds having different patterns of spaced apart notes may include one or more notes having at least one of a different amplitude, a different duration, and a different frequency than at least one other note of a different alarm sound; commanding the speaker to broadcast a sound of the one or more types of sounds may include commanding the speaker to broadcast a sound using a driver associated with control circuitry of the medical treatment device that controls treatment of a patient (e.g., wherein it may be determined whether the speaker was operable to broadcast the sound; thus confirming operation of the driver) and commanding the speaker to broadcast a sound based using a driver associated with circuitry different than the control circuitry of the medical treatment device (e.g., wherein it may be determined whether the speaker was operable to broadcast the sound; thus confirming operation of the additional driver); commanding the speaker to broadcast a sound of the one or more types of sounds may include commanding a primary speaker to broadcast a sound (e.g., wherein it may be determined whether the primary speaker was operable to broadcast the sound and commanding a backup speaker to broadcast a sound (e.g., wherein it may be determined whether the backup speaker was operable to broadcast the sound); the medical treatment device may be an extracorporeal blood treatment apparatus; and/or the processing circuitry may be configured for, or the method may include, alarming or allowing the medical treatment device to be placed in a mode to provide treatment based on whether the speaker was operable to broadcast the sound and whether the sound was audible to a user.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
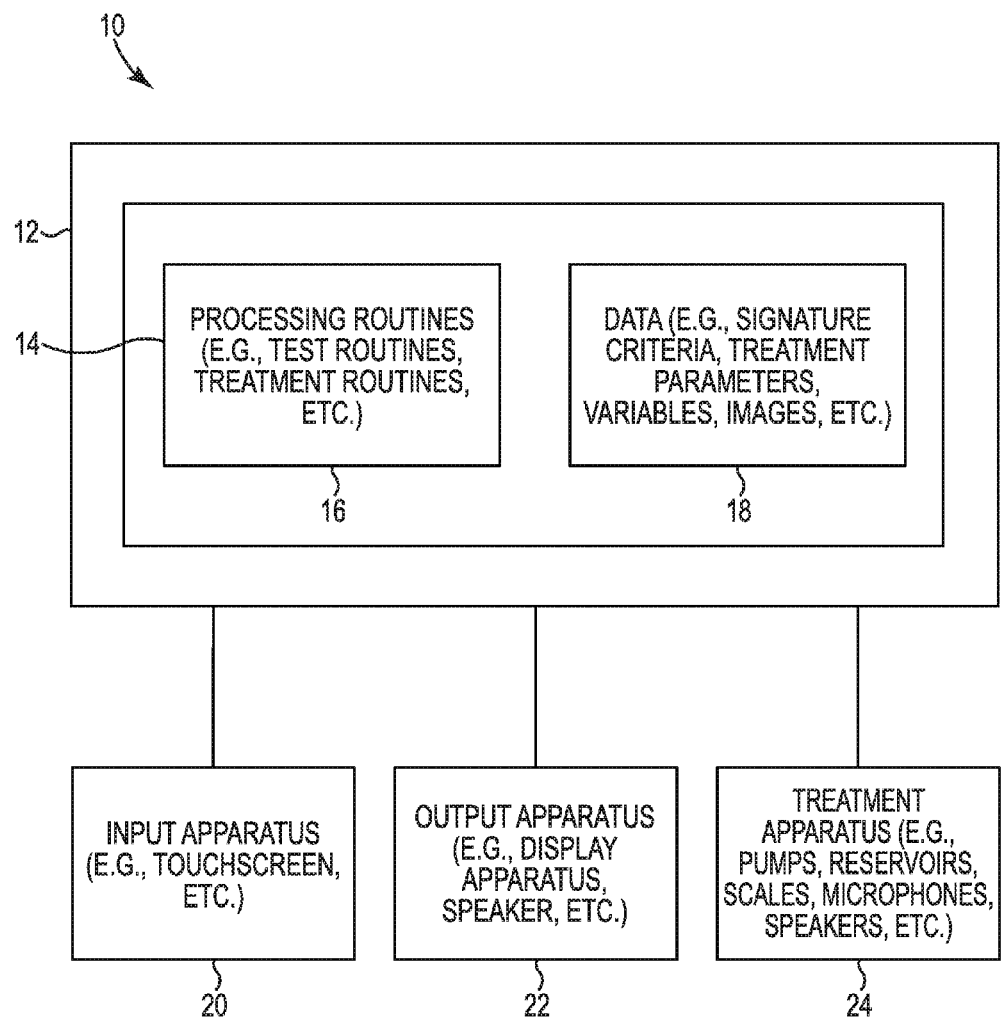
FIG. 1 is a block diagram of an exemplary medical treatment device including input apparatus, output apparatus (e.g., display apparatus), and treatment apparatus that may include speaker sound confirmation functionality as described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary devices and methods providing speaker confirmation functionality for use in medical treatments such as, e.g., extracorporeal blood treatment, shall be described with reference to FIGS. 1-8. It will be apparent to one skilled in the art that elements or processes from one embodiment may be used in combination with elements or processes of the other embodiments, and that the possible embodiments of such devices and methods using combinations of features set forth herein is not limited to the specific embodiments shown in the figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary devices (e.g., systems) and/or methods may use, or utilize, speaker confirmation functionality as described herein for an extracorporeal blood treatment system or for any other medical treatment device or system (e.g., intensive care unit ventilator systems, infusion pump systems, dialysis systems, patient monitoring systems, blood pressure monitoring systems, peritoneal dialysis systems, etc.) that may benefit therefrom. Such speaker confirmation functionality may provide a process for independent confirmation that an alarm sound was broadcast and was audible to a user (e.g., may be heard by a user). For example, such an alarm sound may be broadcast by any number of types of speakers (e.g., a primary speaker of a medical treatment device, a backup speaker of a medical treatment device, etc.).

Exemplary medical treatment device 10 depicted in FIG. 1 may be used to execute, or perform, the exemplary methods and/or processes described herein. In at least one embodiment, the device 10 may be a machine for the extracorporeal treatment of blood (e.g., see FIG. 2). The device 10 could, for example, alternatively be a blood processing device or a blood component preparation device or other medical apparatus for fluid delivery/collection.

As shown, the exemplary medical treatment device 10 includes computing apparatus 12 (e.g., one or more processors). The computing apparatus 12 may be configured to receive input from input apparatus 20 and transmit output to output apparatus 22 (e.g., display apparatus). Further, the computing apparatus 12 may include data storage 14 (e.g., non-volatile and volatile memory). Data storage 14 may allow for access to processing programs or routines 16 (e.g., treatment control routines, test routines, sound detection routines, routines for the displaying information, etc.) and one or more other types of data 18 (e.g., operation parameters, sound signature criteria for use in providing speaker sound confirmation functionality, boot files, graphical elements, variables, images, macros, etc.) that may be employed to perform, or carry out, exemplary methods and/or processes (e.g., displaying graphical user interfaces, accessing data stored in memory for use in providing speaker sound confirmation, issuing alarms, running a treatment, determining problems with a treatment, detecting system malfunctions, filtering processes, sound detection, notifying operators/users of problems, etc.) for use in performing a medical treatment.

The computing apparatus 12 may be operatively coupled to the input apparatus 20 and the output apparatus 22 to, e.g., transmit data to and from each of the input apparatus 20 and the output apparatus 22. For example, the computing apparatus 12 may be electrically coupled to each of the input apparatus 20 and the output apparatus 22 using, e.g., analog electrical connections, digital electrical connections, wireless connections, bus-based connections, etc. An operator may provide input to the input apparatus 20 to manipulate, or modify, a medical treatment.

Further, various devices and apparatus may be operatively coupled to the computing apparatus 12 to be used with the computing apparatus 12 to perform one or more medical procedures/treatments as well as the functionality, methods, and/or logic described herein. As shown, the device 10 may include input apparatus 20, output apparatus 22 (e.g., display apparatus, speakers, etc.), and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. A touchscreen may overlay a display apparatus such that, e.g., an operator may use the touchscreen to interact (e.g., by touch) with a graphical user interface displayed on the display apparatus. For example, the input apparatus 20 may allow an operator to interact with a graphical user interface including an alarm region containing, or depicting, information related to the issued alarm. Further, for example, the input apparatus 20 may allow an operator to interact with a graphical user interface to, e.g., modify one or more treatment parameters, change the type of treatment, etc. when used in conjunction with the display apparatus (e.g., displaying the graphical user interface).

A display apparatus of output apparatus 22 may include any apparatus capable of displaying information to an operator, such as a graphical user interface, etc., to perform the functionality, methods, and/or logic described herein. For example, the display apparatus may include a liquid crystal display, an organic light-emitting diode screen, a touchscreen, a cathode ray tube display, etc.

The processing programs or routines 16 may include programs or routines for performing computational mathematics, matrix mathematics, standardization algorithms, comparison algorithms, or any other processing required to implement one or more exemplary methods and/or processes described herein. Data 18 may include, for example, operational parameters, treatment control files, graphical user interfaces, alarm data, sound signature information (e.g., signature criteria), fluid data, flow rates, fluid volumes, notifications, pressures, pressure limits, blood flow, blood flow limits, fluid removal rates, fluid removal limits, target blood temperatures, blood temperature limits, heuristics indicative of malfunction, results from one or more processing programs or routines employed according to the disclosure herein, or any other data that may be necessary for carrying out the one and/or more processes or methods described herein.

In one or more embodiments, the medical treatment device 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

Programs used to implement the methods and/or processes described herein may be provided using any programmable language, or code, e.g., a high level procedural and/or object orientated programming language, or code, that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the medical treatment device 10 may be implemented using a computer readable storage medium, configured with a computer program, where the storage medium so configured causes the computer to operate in a specific and predefined manner to perform functions described herein. Further, in at least one embodiment, the device 10 may be described as being implemented by logic (e.g., object code) encoded in one or more non-transitory media that includes code for execution and, when executed by a processor, is operable to perform operations such as the methods, processes, and/or functionality described herein.

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., power system control, safety system processing, graphics processing, control of a medical treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by an operator.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof (e.g., also considered agents as discussed herein). For example, various aspects of the techniques may be implemented within one or more processors, including one or more microprocessors, DSPs, ASICs, FPGAs, or any other equivalent integrated or discrete logic circuitry, as well as any combinations of such components, or other devices (e.g., also considered agents as discussed herein). The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The treatment apparatus 24 may include any apparatus used by an exemplary medical treatment device (e.g., an extracorporeal blood treatment system capable of performing extracorporeal blood treatments), such as, e.g., speakers, microphones, pumps, reservoirs, scales, treatment sets, filters, pressure sensors, etc. For example, the treatment apparatus 24 may include one or more elements, or components, of the extracorporeal blood treatment system 100 described herein with reference to FIG. 2.

At least in one embodiment, the medical treatment device 10 may perform one or more medical treatments under control of computing apparatus 12, and may include one or more acoustic transducers or microphones (e.g., a microphone to monitor speaker sound for use in providing speaker sound confirmation functionality as described herein, a microphone as an input device for the computing apparatus 12 to provide recorded audio files, etc.). For example, such microphones may be controlled by computing apparatus 12 to be operable for any desired period of time (e.g., such microphones may be on at all times when the machine is turned on, such microphones may be on or operable for a short period of time, such microphones may be used to monitor sound during a time period when the speaker is expected to broadcast a sound, etc.). Such microphones may be any suitable acoustic transducer for use in converting sound wave vibrations into an electrical sound signal that may be stored and/or analyzed, such as, for example, in providing speaker sound confirmation functionality as described herein. Further, the electrical sound signal may be sampled, analog to digital conversion may be used to provide a digital representation thereof, etc., for example, to provide a sound signal that may be monitored, stored, and/or analyzed.

At least in one embodiment, the device 10 may perform one or more medical treatments under control of computing apparatus 12, and may include one or more speakers (e.g., a primary speaker, a backup speaker, etc.) for sounding or broadcasting an alarm sound under control of computing apparatus 12. Such speakers may be of any suitable form and driven for broadcasting sounds in any suitable manner. For example, digital to analog converters may be used to provide an analog signal for driving the speaker based on a digital command issued by computing apparatus 12. Further, for example, codecs may be used for providing an analog signal for driving the speaker. As the speaker sound confirmation functionality described herein is independent of the actual speaker configuration (e.g., independent of components of the speaker, of the speaker driver, speaker power circuitry, etc.), such confirmation functionality described herein may be applied to any speaker configuration commanded to broadcast a sound.

For example, a speaker may be commanded by a treatment control processor to issue an alarm sound (e.g., a driver under control of a treatment control processor may be commanded to drive the speaker to broadcast one or more sounds, such as, a test sound, an alarm sound, etc.). Further, for example, a speaker may be commanded by one or more processors, unrelated and or independent of the treatment control processor, to issue an alarm sound (e.g., a driver under control of a processor independent of the treatment control processor, such as, a safety processor, may be commanded to drive the speaker to broadcast one or more sounds, such as, a test sound, an alarm sound, etc.). For example, the medical treatment device 10 may include a primary speaker controllable by a treatment control processor (e.g., a processor controlling treatment of a patient and capable of detecting alarm situations that may require commanding an alarm sound to be broadcast (e.g., produced, made audible, etc.). Further, for example, the medical treatment device 10 may include a backup speaker controllable by a safety system processor (e.g., a processor configured to provide redundancy, monitor operation of treatment control, etc.). For example, a backup speaker may be used if a primary speaker experiences problems (e.g., sound confirmation functionality has detected a problem with the primary speaker, a sound commanded to be broadcast has not been confirmed, sound commanded to be broadcast has been detected as being inaudible such that a user may not hear the alarm sound, etc.).

Medical treatment device 10 (e.g., devices providing medical therapies) may be configured (e.g., such as with use of a safety system processor) to perform, for example, power on self-tests or various other on-going tests (e.g., when the medical treatment device is powered on by a user, after the device is power cycled, as part of ongoing system self-test to ensure the device operates safely, etc.). For example, one or more of such tests may include: supply voltage tests; clock accuracy tests, battery health checks; and tests such as, one or more tests to determine proper functioning of device speakers. For example, speaker sound confirmation tests to determine proper functioning of alarms (e.g., speaker functionality, speaker connectivity functionality, speaker driver functionality, etc.) may be performed under control of computing apparatus 12.

For example, when medical treatment device 10 is powered on, a power on self-test (a POST test) may be performed to confirm that a primary speaker and a backup speaker are operable to broadcast a test sound and confirm that the test sound was audible to a user (e.g., single short beeps at different frequencies may be broadcast). Further, for example, when medical treatment device 10 is powered on, one or more audible alarm confirmation tests may also be performed to confirm that at least a primary speaker is operable to broadcast one or more alarm sounds (e.g., wherein such alarm sounds may be a plurality of different types of alarm sounds, such as high priority, medium priority, and low priority alarms), and to confirm that such alarms were audible to a user.

The algorithms described herein to perform speaker sound confirmation may be called into operation from any operational mode of the medical treatment device 10. For example, such functionality may be used in a POST test mode, may be used in and/or during delivery of therapy mode, may be used in a service mode, or at any other time as needed to detect presence of audio (e.g., to determine if the speaker was operable to broadcast a sound and whether the sound was audible to a user).

As used herein, when it is determined that an alarm sound is audible to a user, the alarm sound is determined to exceed a certain amplitude or volume level capable of being heard by a user. In other words, an inaudible alarm sound may be confirmed as being broadcast, but may not meet the threshold of being heard by a user (e.g., the sound may not be loud enough, the amplitude of the sound may not be great enough to be heard or may not exceed some minimum threshold amplitude level).

Figure 3:
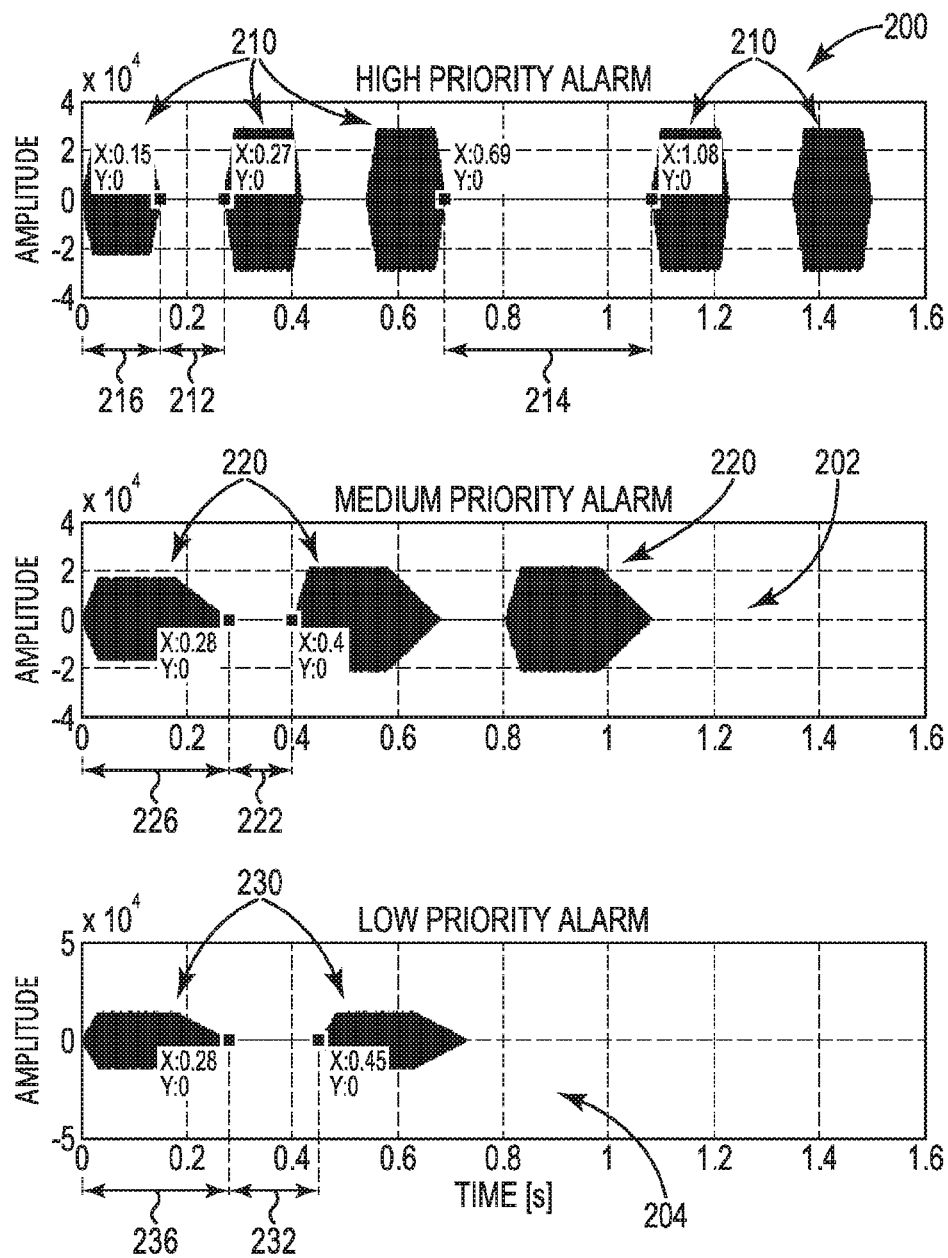
FIG. 3 is an exemplary graphical illustration of a plurality of alarm sounds, for example, for use in describing speaker sound confirmation.
Figure 4:
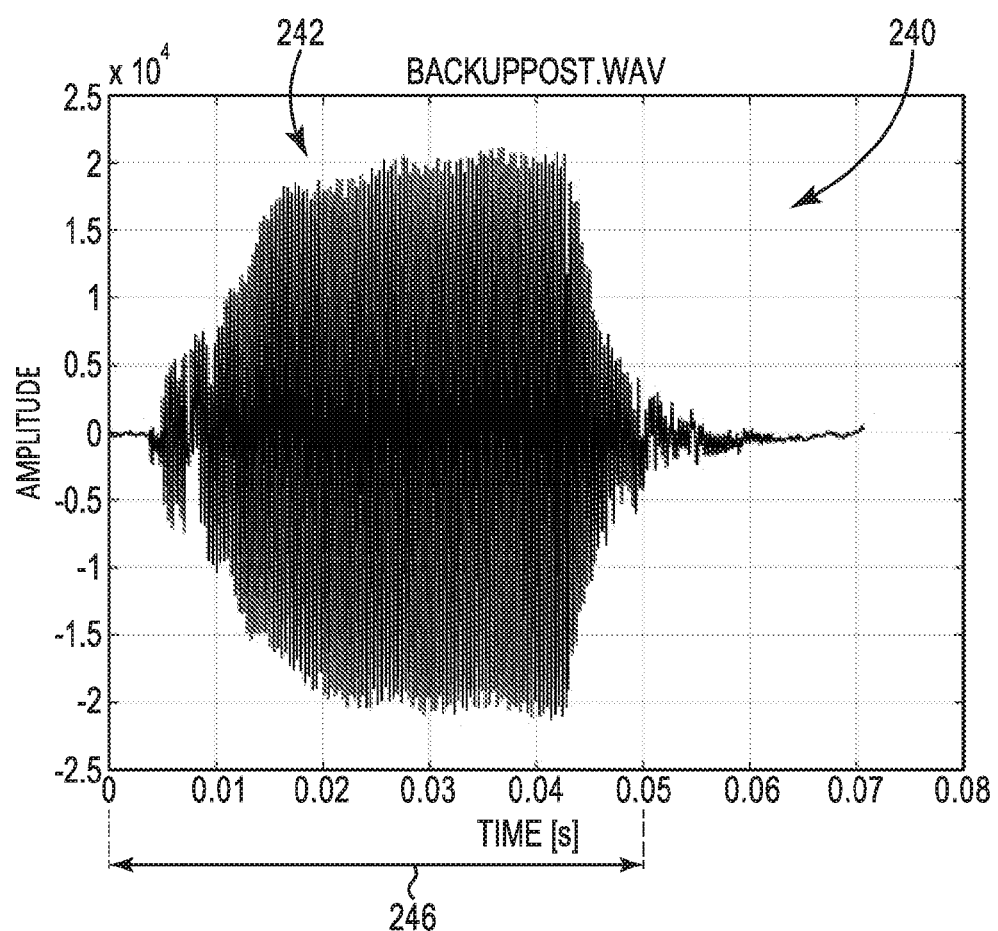
FIG. 4 is an exemplary graphical illustration of a test sound, for example, for use in describing speaker sound confirmation.

As illustrated in FIGS. 3-4, the speaker of the medical treatment device 10 may be configured to broadcast one or more types of sounds. Although any sound may be broadcast, in one or more embodiments, the speaker may be configured to at least broadcast alarm sounds and test sounds. For example, FIG. 3 shows a graphical illustration of one exemplary embodiment of a plurality of different types of alarm sounds including a high priority alarm 200, a medium priority alarm 202, and a low priority alarm 204. Each of the alarm sounds shown in FIG. 3 include a plurality of spaced apart notes with each note having a duration, an amplitude, and a frequency (i.e., a fundamental frequency).

For example, with reference FIG. 3, the high priority alarm 200 includes five notes including a first set of three equally spaced notes 210 (i.e., separated by a time 212, such as, for example, 120 ms) and a second set of two notes having the same spacing (i.e., separated by time 212, such as, for example, 120 ms) as the first set. However, the first set of notes is spaced from the second set by a time duration 214 (e.g., 390 ms) that is longer than the spacing time 212 between the notes within the first and second set. Each of the notes 210 has a duration time 216 (e.g., 150 ms with a leading ramp time of 25 ms and a falling ramp time of 25 ms). The frequency (e.g., fundamental frequency) of such notes 210 may be about 262 Hz (e.g., a C-note). The amplitude of the first note of the high priority alarm 200 is shown to be slightly less than the other notes 210 of the high priority alarm 200.

Further, for example, with reference FIG. 3, the medium priority alarm 202 includes three equally spaced notes 220 (i.e., separated by a time 222, such as, for example, 120 ms). Each of the notes 220 has a duration time 226 (e.g., 280 ms with a leading ramp time of 30 ms and a falling ramp time of 100 ms). The frequency (e.g., fundamental frequency) of such notes 220 may be about 262 Hz (e.g., a C-note). The amplitude of the first note 220 of the medium priority alarm 202 is shown to be slightly less than the other notes 220 of the medium priority alarm 202. Still further, for example, with reference FIG. 3, the low priority alarm 204 includes two spaced notes 230 (i.e., separated by a time 232, such as, for example, 170 ms). Each of the notes 230 has a duration time 236 (e.g., 280 ms with a leading ramp time of 30 ms and a falling ramp time of 100 ms). The frequency (e.g., fundamental frequency) of such notes 230 may be about 262 Hz (e.g., a C-note). The amplitudes of the notes 230 of the low priority alarm 200 are substantially the same.

One will recognize that the alarm sounds may include varied characteristics within an alarm sound and between alarm sounds, and that the present disclosure is not limited to any particular alarm sound profile or profiles. For example, the duration of notes may differ, the number of notes may differ, the frequency of notes may differ, the spacing between notes may differ, and the duration of the notes may differ, within each of the alarm sounds of a plurality of types of alarm sounds and also between such types of alarm sounds.

Further, for example, FIG. 4 shows a graphical illustration of one exemplary embodiment of a test sound 240 (e.g., a beep used in a POST test to confirm operation of one or more speakers). For example, a test sound may include a note (or a plurality of notes) having a duration, an amplitude, and a frequency (i.e., a fundamental frequency). As shown in FIG. 4, for example, the note 242 of test sound 240 has a duration time 246 (e.g., about 50 ms with a leading ramp time of about 10 ms and a falling ramp time of about 12.5 ms). The frequency (e.g., fundamental frequency) of the note 242 may be about 2777 Hz (e.g., a higher pitch than the C-note). The amplitude of the test note is also shown in FIG. 4.

One will recognize that the test sound may be of varied characteristics, and that the present disclosure is not limited to any particular test sound profile or profiles. For example, the duration of note may differ, the number of notes may differ (e.g., two notes instead of one with spacing therebetween like an alarm sound), the frequency of notes may differ, etc.

As such, for example, as shown in FIGS. 3-4, each type of sound (e.g., an alarm sound, a test sound, etc.) is associated with a predefined sound signature. Such sound signatures are used by the medical treatment device so that when broadcast as the result of an alarm situation, a user can distinguish between different types of alarm sounds, different test sounds, etc. Such sound signatures include criteria that may be used to provide speaker sound detection functionality (e.g., for determining if the speaker was operable to broadcast the sound and whether the sound was audible to a user). For example, as further described herein, the sound signature corresponding to an alarm sound may include criteria based at least on the amplitude and duration of at least two notes of a plurality of spaced apart notes. Further, for example, as further described herein, the sound signature corresponding to a test sound may include criteria based on the amplitude and duration of the note thereof.

The exemplary devices (e.g., systems), and exemplary methods performed, or used, by such exemplary systems, described herein which may provide speaker sound detection functionality may include systems such as, e.g., dialysis systems. The general term "dialysis" as used herein includes hemodialysis, hemofiltration, hemodiafiltration, hemoperfusion, liver dialysis, and therapeutic plasma exchange (TPE), among other similar treatment procedures. In dialysis generally, blood is taken out of the body and exposed to a treatment device to separate substances therefrom and/or to add substances thereto, and is then returned to the body. Although extracorporeal blood treatment systems capable of performing general dialysis (as defined above, including TPE) shall be described herein with reference to the exemplary extracorporeal blood treatment system of FIG. 2, other systems such as those for infusion of drugs, performance of continuous renal replacement therapy (CRRT), extracorporeal membrane oxygenation (ECMO), hemoperfusion, liver dialysis, apheresis, TPE, etc. may benefit from the devices (e.g., systems or apparatus) or methods described herein and the present disclosure is not limited to any particular treatment system.

Figure 2:
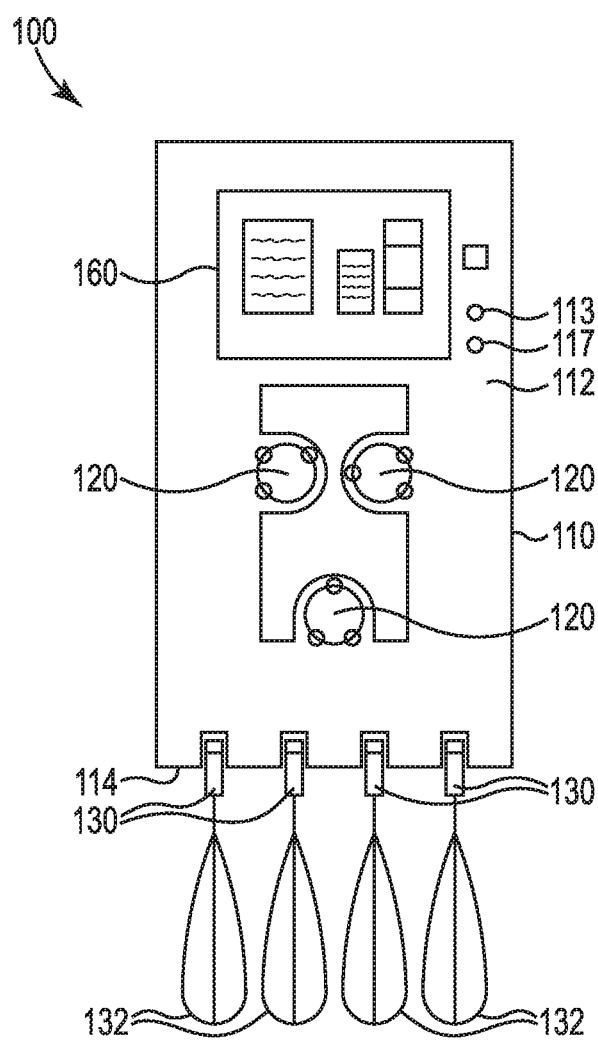
FIG. 2 is an illustration of an exemplary extracorporeal blood treatment system that may include speaker sound confirmation functionality as described herein.

Referring to FIG. 2, one illustrative embodiment of an extracorporeal blood treatment system, or apparatus, 100 is depicted which includes all the features described with reference to the device 10 shown in FIG. 1. The system 100 includes a housing 110 having a front face 112. The system 100 further includes one or more pumps 120 used to move liquids through the system as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc.

The extracorporeal blood treatment system 100 also includes, in one or more embodiments, a display 160 used to convey information to an operator or user. The display 160 may also serve as an input device if, e.g., the display 160 is in the form of a touchscreen. Further, for example, the system 100 may include one or more speakers 113 for broadcasting sounds, such as, for example, alarm sounds, test sounds, etc. Still further, for example, system 100 may include one or more microphones 117 for input of information by a user, for monitoring broadcast sounds for use in speaker sound confirmation functionality, etc.

The extracorporeal blood treatment system 100 also includes one or more reservoir scales 130, each of which is configured to hold and weigh a reservoir 132. The reservoir scales 130 are positioned below a bottom end 114 of the housing 110, at least in part because the reservoirs 132 are typically attached to and hang from the reservoir scales 130.

For example, system 100 may be implemented by a generalized system architecture that, for example, may include a power system controller for use in providing power to various components of the medical treatment device, a treatment control processor, for example, configured to control the performance of a treatment on a patient, and a safety processor, for example, configured to watch or monitor the treatment control processor or operations controlled thereby which may all be coupled in a communicative network.

System 100, such as shown in FIG. 2, typically continuously examines how a device is performing as part of a power on self-test and as part of ongoing system self-test to ensure the device continues to operate safely. For example, problems may be detected by performing one or more various tests (e.g., such as machine malfunctions, therapy problems, etc.) resulting in one or more types of alarm sounds (e.g., high priority alarms, low priority alarms, medium priority alarms, perfusion alarms, general system alarms, etc.). Further, for example, various speaker sound confirmation tests may also be performed such as described herein (e.g., POST speaker tests, ongoing speaker tests to test the continuity of a speaker each time it is turned on, etc.).

Figure 5:
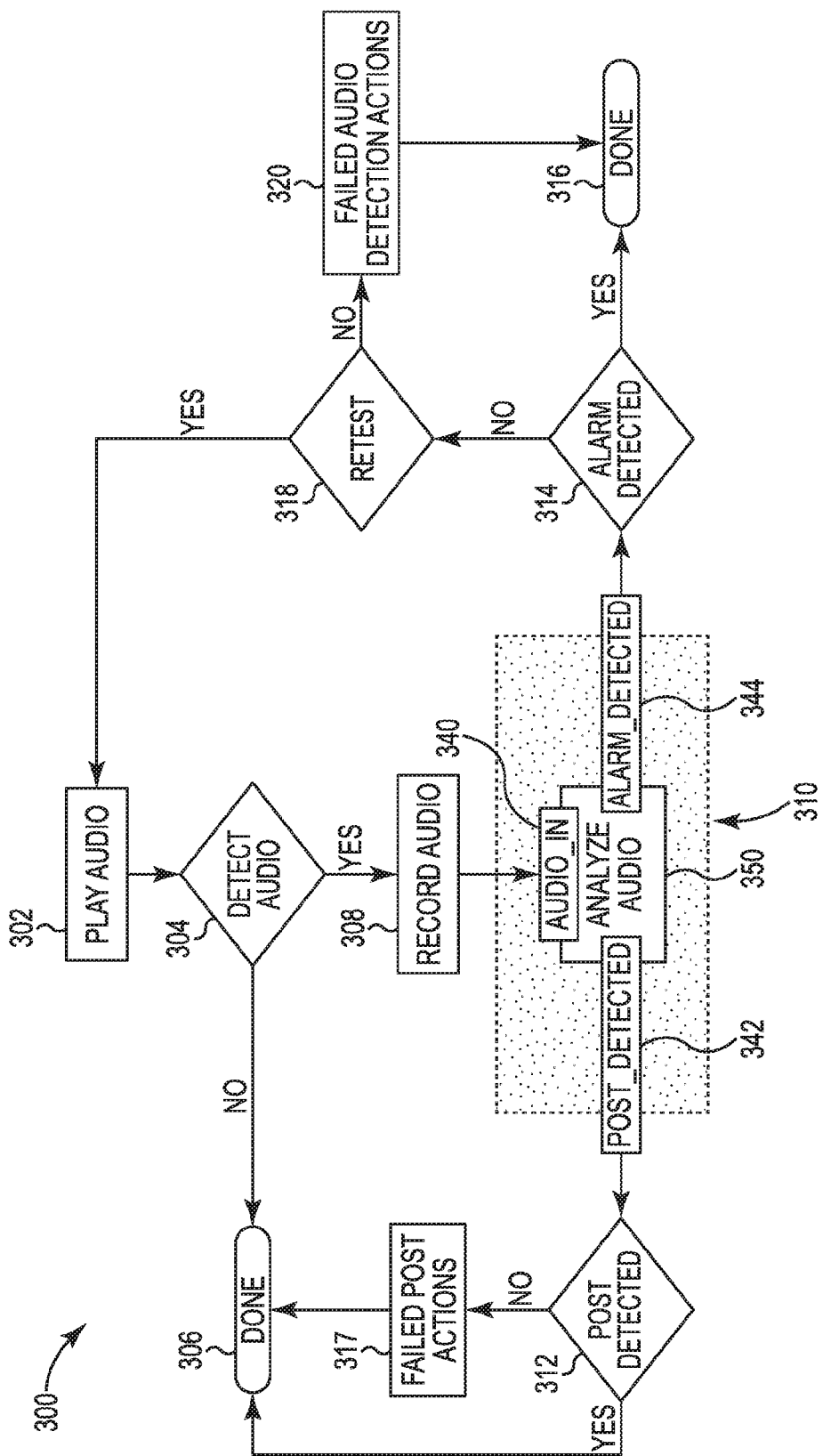
FIG. 5 is a block diagram depicting one exemplary embodiment of a method including speaker sound confirmation for a medical treatment device, for example, such as shown generally in FIGS. 1-2.

A method 300 for a medical treatment device that provides speaker sound confirmation functionality is shown in FIG. 5 and shall be described with reference to one or more of the figures (e.g., FIGS. 1-4 and 6-8). For example, the method 300 may include playing a type of sound (block 302) (e.g., audio, such as one of a plurality of alarm sounds, a test sound, etc.). For example, as described herein, playing the sound may be initiated by detection of an alarm condition, running a POST test, etc. For example, such an audio sound may be played during therapy, during POST tests, in service mode, etc. Further, for example, the audio may be played under control of a treatment control processor, safety control processor, or any other control circuitry of a medical treatment device (e.g., device 10, system 100, etc.).

In one embodiment, a determination may be made as to whether or not to detect the audio being played (block 304) (e.g., whether the method 300 needs to record audio (block 308) and provide speaker sound detection or whether it does not need to be carried out and the process is completed (block 306)). For example, in one or more embodiments, confirmation of speaker sound may become unnecessary, and the method 300 may be done (block 306) even though audio is played (block 302). For example, the audio being played may be a high priority audio alarm (e.g., see FIG. 3) that has repeated itself multiple times. If, for example, the speaker sound confirmation process determined after the high priority audio alarm was played the first time that the speaker was operable to broadcast the high priority audio alarm and that the alarm was audible to a user, then when the high priority audio alarm is played the second, or third, time, the process 300 may determine that it is unnecessary to further confirm broadcast of the high priority audio alarm.

If, however, it is determined that speaker sound confirmation is to be conducted with respect to the audio played (block 302), then, according to decision block 304, the acoustic transducer is used for recording the audio played (block 308). For example, the acoustic transducer may be used to generate a sound signal representative of the sound of the played audio when broadcast by the speaker. For example, the acoustic transducer may be configured to record the audio played or sound during a time period when the speaker is expected to broadcast the sound. For example, if the played audio is a test sound, the acoustic transducer may be configured for a time period corresponding to the duration of a test sound (e.g., including a certain amount of time before and after the expected broadcast time) to record sound. Likewise, for example, if the played audio is a sound, such as an alarm sound, the acoustic transducer may be configured for a time period corresponding to the duration of the alarm sound (e.g., including a certain time before and after the expected broadcast time of the alarm sound) to record sound.

Figure 6:
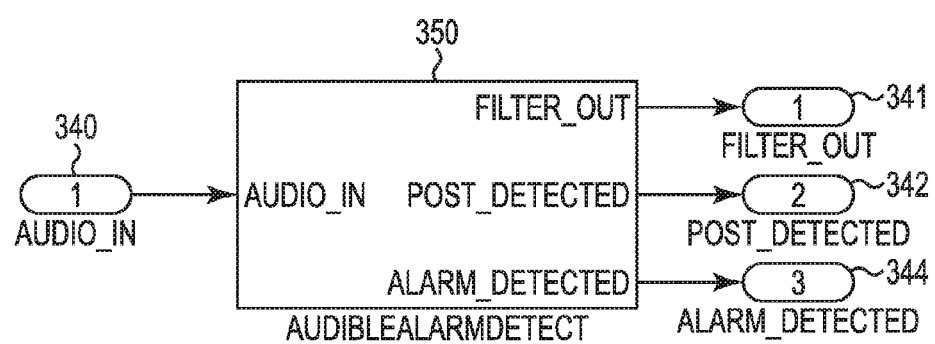
FIG. 6 is an input/output block diagram showing one exemplary embodiment of speaker sound confirmation functionality for a medical treatment device, for example, such as shown generally in FIGS. 1-2.

The recorded audio may be stored for analysis by a sound detection algorithm or process (block 310) or the audio may be presented, in real time, for analysis by a sound detection algorithm or process (block 310) (e.g., may be stored in nonvolatile memory, volatile memory, etc.; may be presented for analysis in real time, within a certain timeframe, etc.; such analysis may be conducted as commanded by computing apparatus of the medical treatment device; etc.). Generally, in one or more embodiments, the audio input 340 may be any input representative of the sound signal (e.g., sensed by the acoustic transducer), including, for example, a raw audio signal, a compressed audio signal (e.g., compressed using MP3, AAC, FLAC, WMA, etc.), content of a compressed audio signal (e.g., the frequency content and loudness contours from an MP3 compressed audio signal), etc. At least in one embodiment as shown in FIG. 5, and also in the input/output diagram of FIG. 6, audio input (AUDIO_IN) 340 (e.g., a test sound or an alarm sound), for example, such as after preprocessing using scaling, filtering, etc., may be operated upon by an analysis algorithm 350 of sound detection algorithm 310 resulting in an output indicative of whether the speaker was operable to broadcast the sound and whether the sound was audible to a user (e.g., whether a test sound commanded to be broadcast was actually broadcast by the speaker and was actually audible to a user (POST_DETECTED 342) or whether an alarm sound commanded to be broadcast was actually broadcast by the speaker and was actually audible to a user (ALARM_DETECTED 344). Further, as shown in FIG. 6, a filtered signal output (FILTER_OUT 341) may be provided as an output for use in one or other processes of the system (e.g., diagnostics, etc.).

If, for example, in one or more embodiments, the output or decision 342 of the analysis algorithm 350 determines that a test sound commanded to be broadcast (block 302) was detected confirming that the speaker was operable to broadcast the test sound and that the test sound was audible to a user (block 312), then the method 300 is completed (block 306). If, for example, in one or more embodiments, the output or decision 342 of the analysis algorithm 350 determines that a test sound commanded to be broadcast (block 302) was not detected confirming that the speaker was not operable to broadcast the test sound or that the test sound is not audible to a user (block 312), then actions are taken in view of a failed sound test (block 317). For example, such actions may include replaying the test sound and rerunning sound detection, declaring a speaker malfunction and invoking a backup speaker, providing a visual alarm of a system malfunction, etc.

If, for example, in one or more embodiments, the output or decision 344 of the analysis algorithm 350 determines that an alarm sound commanded to be broadcast (block 302) was detected confirming that the speaker was operable to broadcast the alarm sound and that the alarm sound was audible to a user (block 314), then the method 300 is completed (block 316). If, for example, in one or more embodiments, the output or decision 344 of the analysis algorithm 350 determines that an audio alarm commanded to be broadcast (block 302) was not detected confirming that the speaker was not operable to broadcast the alarm sound or that the alarm sound is not audible to a user (block 314), then actions are taken in view of the failed detection (block 314). For example, it may be determined whether a retest 318 should be performed. If, for example, a retest 318 is to be performed, then the process restarts by replaying the audio alarm. If it is decided to not retest 318, then actions are taken in view of a failed audio alarm sound test (block 320). For example, such actions may include declaring a speaker malfunction and invoking a backup speaker, providing a visual alarm of a system malfunction, etc. Once such actions (block 320) are taken, method 300 is complete (block 316).

In one or more embodiments, the algorithm or process 310 may be designed to be called from therapy, POST, or service modes as needed to detect audio from a prerecorded file. At least in one embodiment, the algorithm does not need to process the audio in real time or need to be run after sound has been determined to be audible to a user. After being called, and after the algorithm 310 is performed, the caller decides which action needs to be taken, such as rerunning the test on a new set of audio files, declaring a speaker malfunction and invoking a backup speaker, etc.

Figure 7:
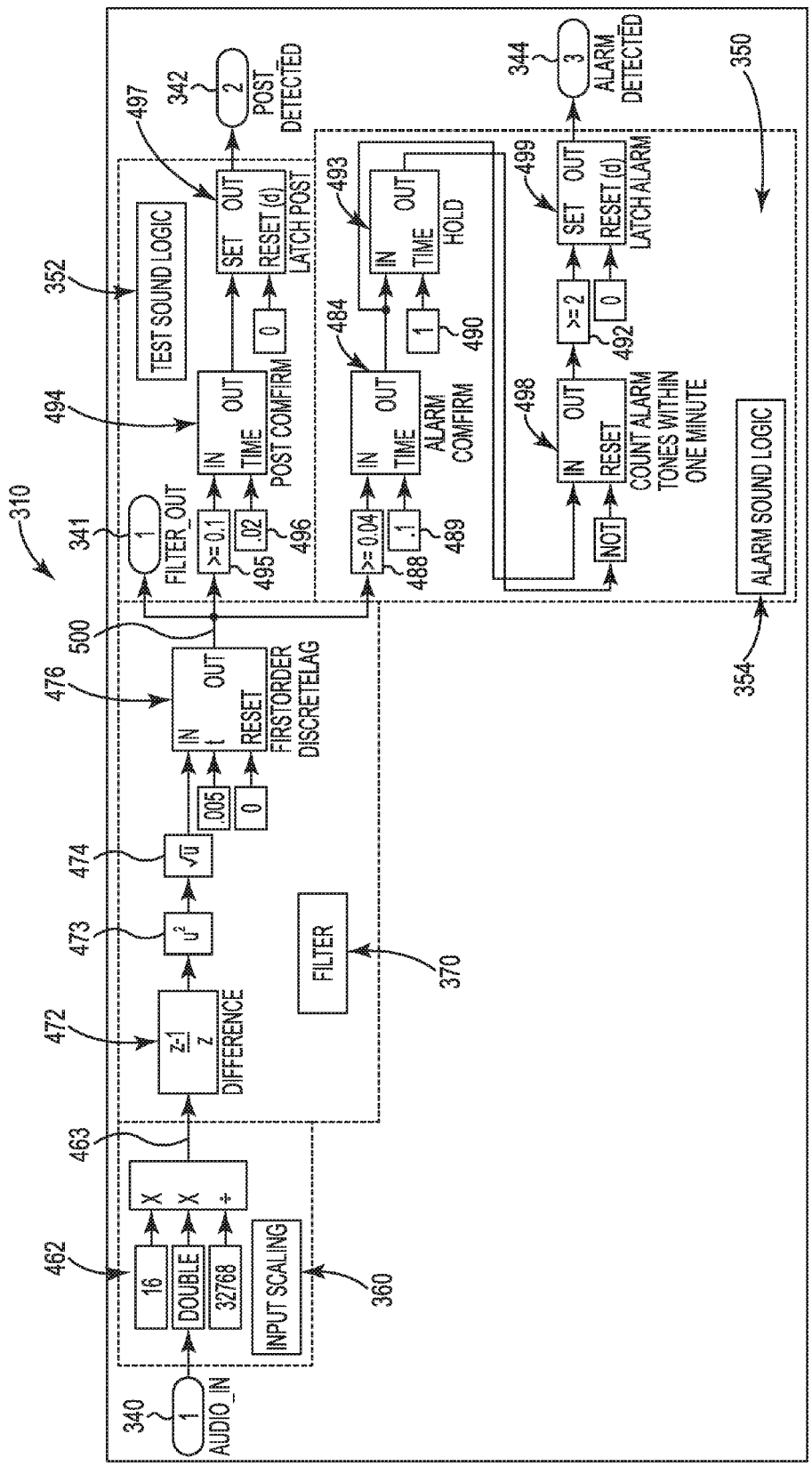
FIG. 7 is a block diagram depicting generally, and also one exemplary implementation embodiment, for providing speaker sound confirmation for a medical treatment device, for example, such as shown generally in FIGS. 1-2.

The analysis algorithm 350 of the algorithm or process 310, such as shown generally by the larger blocks of FIG. 7 (e.g., 350, 360, and 370), and also shown more specifically with respect to one or more particular implementations of the algorithm within the blocks of the block diagram of FIG. 7 (e.g., a filter implementation, a scaling implementation, logic for detecting a test sound, logic for detecting an alarm sound, etc.), uses the sound signatures corresponding to the different types of sounds (e.g., test sounds, one or more alarm sounds of a plurality of alarm sounds, etc.) to determine if the speaker was operable to broadcast the sound and whether the sound is audible to a user (e.g., is greater than a desired audible threshold such that a user would be able to hear the sound). For example, the algorithm 350 confirms whether a sound signature associated with a sound commanded to be broadcast is present within a sound recording taken or recorded during a time period when the speaker was expected to broadcast the sound. Various criteria of the sound signatures are used to make a determination of whether the sound signature is present within the sound recording.

For example, such criteria of the sound signatures may include criteria based upon duration of notes within the sound (e.g., a test sound note, a note or one or more notes of an alarm sound, etc.), amplitude of notes within the sound, spacing between one or more notes of the sound (e.g., spacing between one or more notes of an alarm sound), etc. However, at least in one embodiment, the criteria of the sound signature used to make a determination of whether the sound signature is present within the sound recording are independent of frequency (e.g., thus reducing the complexity of computations used to make the determination).

For example, as described herein, sound signature criteria used to make the determination of whether the sound signature of an alarm sound is present within the sound recording may include criteria based at least on the amplitude and duration of at least one note of the alarm sound (e.g., at least two notes of a plurality of spaced apart notes). Further, for example, sound signature criteria used to make the determination of whether the sound signature of a test sound is present within the sound recording may include criteria based on the amplitude and duration of the note thereof. At least in one embodiment, separate sound signature criteria for each alarm sound of the plurality of types of alarm sounds may be used to make the determination of whether the sound signature of a commanded alarm sound is present within the sound recording. At least in one or more other embodiments, a common predefined sound signature associated with a plurality of types of alarm sounds may be used to make the determination of whether the sound signature of a commanded alarm sound is present within the sound recording (e.g., the common predefined sound signature may be based on lowest common denominator criteria common to all of the plurality of types of alarm sounds).

For example, where the sound commanded to be broadcast is a test sound, the recorded audio of the sound signal generated by the acoustic transducer during a time period when the speaker is expected to broadcast the test sound (e.g., a scaled and filtered sound signal) is compared to the sound signature including the sound signature criteria (block 352) (e.g., single short beeps at different frequencies may be broadcast by a speaker with all of the beeps having the same test sound signature, or such beeps may have different test sound signatures). At least in one embodiment, for example, the amplitude of the sound signal is compared to an amplitude threshold of the sound signature for the test sound. A test sound may be detected if the amplitude of the sound signal is greater than the amplitude threshold for a time exceeding a duration time threshold of the sound signature. For example, the sound signature criteria may include an amplitude threshold and a duration threshold which when exceeded leads to a confirmation that the speaker commanded to broadcast the test sound was operable to do so and the test sound was audible to the user. For example, if the recorded sound signal includes a signal portion having an amplitude exceeding 45% of normal system volume (e.g., a minimum system volume; which may be used as the amplitude threshold of the sound signature) for at least a half of the duration of the test sound (e.g., a minimum duration, such as 2 ms; which may be used as the duration threshold of the sound signature), a test sound may be detected confirming the speaker was operable to broadcast the test sound and that the test sound would be audible to a user.

Further, for example, single short beeps at different frequencies may be broadcast by a speaker to perform a POST test. All of the beeps may be detectable using the same test sound signature criteria, or each beep may be detectable based on different test sound signature criteria for each beep.

Further, for example, where the sound commanded to be broadcast is an alarm sound of a plurality of different types of alarm sounds and a common predefined sound signature is used, the recorded audio of the sound signal generated by the acoustic transducer during a time period when the speaker is expected to broadcast the alarm sound (e.g., a scaled and filtered sound signal) is compared to the common predefined sound signature including the sound signature criteria (block 354). At least in one embodiment, for example, the amplitude of the sound signal is compared to an amplitude threshold of the common predefined sound signature for the plurality of different types of alarm sounds. One or more notes of the plurality of notes defining the audio alarm may be detected if the amplitude of the sound signal is greater than the amplitude threshold for a time exceeding a duration time threshold of the common predefined sound signature. For example, the common predefined sound signature criteria for detecting a note of an alarm sound may include an amplitude threshold and a duration threshold. If the existence of a predetermined number of detected notes within the recorded sound signal (e.g., determined based on the common predefined sound signal criteria such as amplitude and duration) exceeds a predetermined number of notes within an alarm duration time threshold of the common predefined sound signature, then it is determined that an alarm sound has been detected. Such detection of the alarm sound confirms that the speaker was operable to broadcast the alarm sound and that the alarm sound was audible to a user.

For example, one exemplary common predefined sound signature may include criteria that are satisfied by each of the plurality of types of alarm sounds. For example, as shown in FIG. 3, an amplitude threshold criteria for the common predefined sound signature for high priority alarms, medium priority alarms, and low priority alarms may be an amplitude exceeding 45% of normal system volume (e.g., a minimum system volume; which may be used as a common amplitude threshold for all of the types of alarm sounds).

Further, for example, as shown in FIG. 3, a note duration time threshold for detecting a note for high priority alarms, medium priority alarms, and low priority alarms may be based on the shortest duration of a note used to define such alarms. For example, as shown in FIG. 3, high priority alarm 200 includes notes 210 having the shortest duration (e.g., 150 ms). As such, a note duration time threshold criteria for use in detecting a note of an alarm sound when a common predefined sound signature is used may be 100 ms (e.g., a minimum note time duration; which may be used as a common note time duration threshold for all of the types of alarm sounds).

Still further, for example, as shown in FIG. 3, a predetermined number of notes threshold for detecting an alarm sound for high priority alarms, medium priority alarms, and low priority alarms may be based on the least number of notes used to define such alarms. For example, as shown in FIG. 3, the low priority alarm 204 includes two notes 230.

As such, an alarm sound in this exemplary embodiment cannot be detected until at least two notes have been detected.

Yet still further, for example, as shown in FIG. 3, an alarm duration time threshold for detecting an alarm sound for high priority alarms, medium priority alarms, and low priority alarms may be based on the alarm with the shortest duration. For example, as shown in FIG. 3, the at least two notes in the low priority alarm 204 must be detected within 0.8 seconds. As such, an alarm duration time threshold criteria for use in detecting an alarm sound (e.g., with at least two notes) when a common predefined sound signature is used may be 1 sec (e.g., a minimum alarm time duration; which may be used as a common alarm time duration threshold for all of the types of alarm sounds). In other words, each of the high priority alarm, the medium priority alarm, and the low priority alarm include at least two notes detectable within a minimum alarm time of 1 sec.

Therefore, at least in this illustrative embodiment with this exemplary set of common sound signature criteria for the high priority alarm, the medium priority alarm, and the low priority alarm, the algorithm 354 determines if the recorded sound signal includes signal portions recognizable as notes of an alarm sound (e.g., portions of the sound signal having an amplitude exceeding 45% of normal system volume for at least a note duration time threshold of 100 ms). If at least two signal portions representative of notes exist in the recorded sound signal within a minimum alarm time threshold of 1 sec, then an alarm sound is detected (e.g., confirming the speaker was operable to broadcast the alarm sound and that the alarm sound would be audible to a user).

Further, for example, where the sound commanded to be broadcast is an audio alarm of a plurality of different types of audio alarms and each type of alarm sound has its own separate sound signature, the recorded audio of the sound signal generated by the acoustic transducer during a time period when the speaker is expected to broadcast the alarm sound (e.g., a scaled and filtered sound signal) may be compared to each separate sound signature including the sound signature criteria. For example, such a comparison may be performed using one or more different processes. For example, a comparison of the recorded sound signal may be compared to each of the sound signatures associated with each different type of alarm sound. Further, for example, the same process using a common predefined sound signature may be used to determine the existence of an alarm sound, and therewith, sound signature criteria based on the spacing between notes of different types of alarm sounds may be used to distinguish between the different types of alarm sounds. For example, as shown in FIG. 3, note spacing between high priority alarm notes is varied and includes at least one longer note between the sets of notes which may be used to distinguish the high priority alarm from the other alarms, the note spacing between the medium priority alarm and the low priority alarm is different (e.g., 120 ms versus 170 ms); etc.

Further, for example, when it is desired to distinguish between the type of alarm sounds, other characteristics of the alarms may be used. For example, the overall duration of the alarm sound may be used to distinguish the alarms (e.g., the higher priority alarm having a longer duration than the medium priority alarm, and the medium priority alarm having a longer duration than the low priority alarm), the number of detected notes may be used to distinguish the alarms (e.g., the high priority alarm having more notes than the medium priority alarm, and the medium priority alarm having more notes than the low priority alarm), etc.

As shown in FIG. 7, prior to the analysis algorithm 350 of the algorithm or process 310 being applied, various types of preprocessing may be performed on the audio input 340, such as shown generally in FIG. 7 (e.g., 360 and 370). For example, the audio input 340 may be scaled (block 360) to increase detector sensitivity when needed, for example, at low volumes at the expense of lower audio which may be easier to detect. Further, for example, the scaled signal may be filtered (block 370) using one or more different filter implementations. For example, the signal of interest (e.g., to be compared to the sound signature) may be amplified by taking a derivative thereof, a smoothing filter may be applied, may be averaged over time, may be integrated, etc. One will recognize that various types of preprocessing may be performed with one or more processing types being more beneficial than others to the detection of the broadcast sounds.

One or more exemplary implementations of the algorithm 310 are shown within the blocks of the block diagram of FIG. 7 (e.g., a filter implementation, a scaling implementation, logic for detecting a test sound, logic for detecting an alarm sound, etc.). Although such a more detailed implementation is shown and described, it will be recognized by one skilled in the art that various other implementations using the general concepts described herein may also be used.

As shown in FIG. 7, in one embodiment, a raw audio signal 340 may be presented (e.g., an audio file input as recorded from a microphone; such as, for example, a 16 bit uncompressed pulse code modulated (PCM) audio at 24,000 Hz; although the audio input need not be a raw audio signal as previously described herein) and scaled using input scaling preprocessing 360. For example, such input scaling 462 may include first converting the raw audio signal 342 to a double, and then dividing it by 32,768 to match a −1 to +1 range of the detector used for amplitude comparison. Further, for example, the signal may be scaled by a scaling factor (e.g., 16) to compensate for audio absorbed inside a housing of the medical treatment device. For example, this may increase the detector sensitivity when it's needed at low volumes at the expense of lower audio that may be easier to detect.

The resulting scaled signal 463 may then be presented for filter preprocessing 370. For example, such filter preprocessing 370 may include first filtering the scaled signal 463 by taking the difference and then calculating the amplitude 472-474 (e.g., a difference calculation $(z-1)/z$ is performed; the result is squared and then the square root is taken of the squared result). Further, for example, taking the derivative of the signal may provide a process for amplifying the signal of interest (e.g., the signal portions corresponding to test sounds, notes, etc.) without altering the frequency content.

A second filter 476, for example, may then be applied (e.g., to provide smoothing of the signal). For example, the second filter may be a simple first order filter with the time constant of 0.005 seconds. This may create, for example, a clean amplitude signal (e.g., filtered signal 500) that may be used to detect the presence of an audio sound when comparison is made with the sound signature criteria corresponding thereto.

Figure 8A:
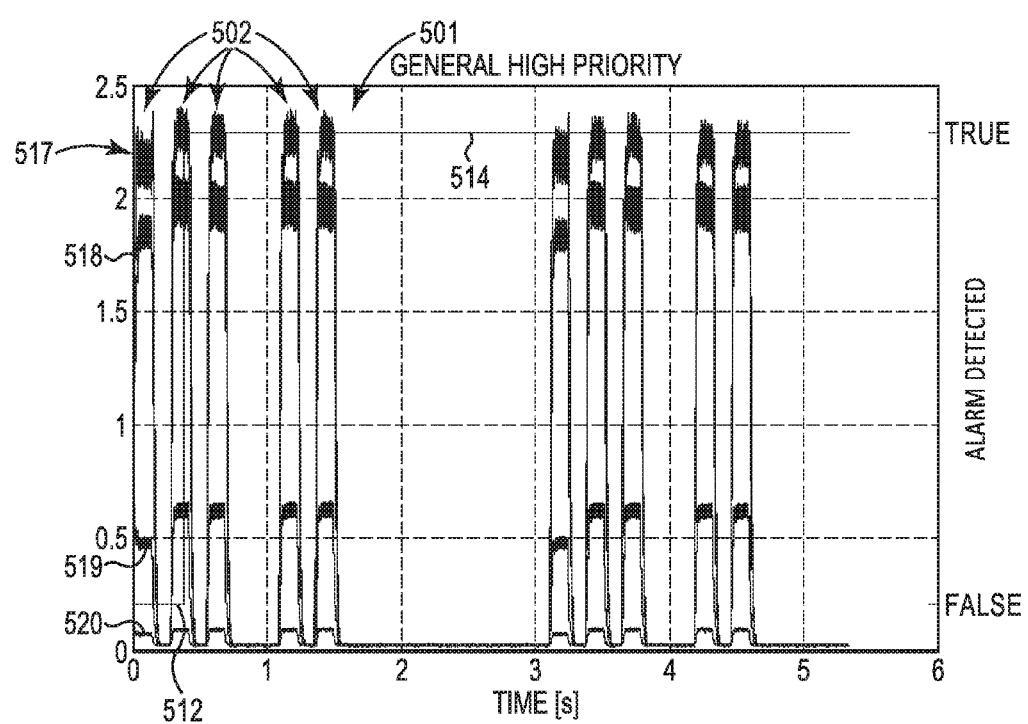
FIGS. 8A-8B are graphical depictions of filtered sound signals for use in describing one or more embodiments of speaker sound confirmation for a medical treatment device, for example, such as shown generally in FIGS. 1-2.
Figure 8B:
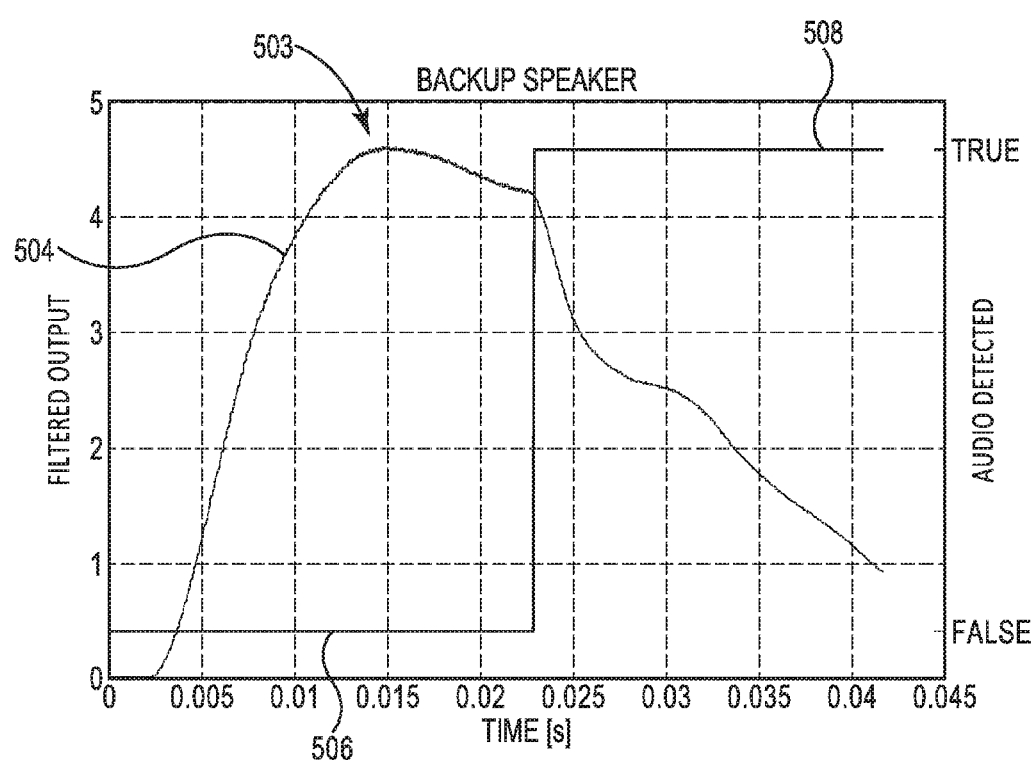

FIG. 8A shows an exemplary filtered signal output 501 after filter preprocessing 370 of a high priority alarm at multiple volume levels in a noisy environment. It is noted that the filtered signal 501 includes signal portions 502 corresponding to notes of the high priority alarm (see, FIG. 3). Filtered signals at four different audible volumes are shown in FIG. 8A (e.g., audible volume 517 being 100% volume, audible volume 518 being 85% volume, audible volume 519 being 65% volume, and audible volume 520 being 45% volume) to illustrate the different levels of audible volume (e.g., those that may be audible to a user and those that may not). FIG. 8B shows an exemplary filtered signal output 503 after filter preprocessing 370 of a test sound (e.g., POST beep) at a volume level in a noisy environment. It is noted that the filtered signal 503 includes a signal portion 504 corresponding to the note of the test sound (see, FIG. 4).

The resulting filtered signal 500 may then be presented for analysis by algorithm 350 to confirm if a sound signature (e.g., corresponding to a test sound, an alarm sound, etc.) is present within the recorded audio. For example, test sound logic 352 may be applied to confirm if a test sound signature is present within the recording and/or alarm sound logic 354 may be applied to confirm if an alarm sound signature is present within the recording.

For example, in at least one embodiment, test sound logic 352 may include using confirm logic 494 to check whether the filtered signal 500 is greater than or equal to 0.1 (e.g., the amplitude threshold criteria 495 of the test sound signature) for 0.02 seconds or 20 ms (e.g., the time duration threshold criteria 496 of the test sound signature). If it is confirmed that the test sound signature is present by confirm logic 494, then the signal is latched and cannot be reset by latch logic 497. A true POST_DETECTED output 342 is provided upon confirmation that the test sound is present. For example, as shown in FIG. 8B, upon satisfaction of the sound signature criteria, a false state 506 is changed to a true state 508 indicative of a determination that the speaker was operable to broadcast the test sound and that the sound would be audible to a user.

Further, for example, in at least one embodiment, alarm sound logic 354 may include using note confirm logic 484 to check whether the filtered signal 500 is greater than or equal to 0.4 (e.g., the note amplitude threshold criteria 488 of the alarm sound signature) for 0.1 seconds or 100 ms (e.g., the note time duration threshold criteria 489 of the alarm sound signature). If it is confirmed that the note sound signature criteria are present by note confirm logic 484, then hold logic 493 holds the note count at one and continues to look for additional signal portions that satisfy the note sound signature criteria within 1 second (e.g., the alarm time duration threshold criteria 490 of the alarm sound signature). At the same time as hold logic 493 stores a note count when a note is confirmed as being present, such a note count is also provided to count logic 498.

If two or more notes (e.g., a predetermined number of notes criteria 492 of the alarm sound signature) are not confirmed to be present within the alarm time duration threshold criteria 490 (e.g., 1 second), then a reset of the count logic 498 is performed under command of hold logic 493. The logic may then continue to look for signal portions that satisfy the note sound signature criteria for a time period (e.g., 1 minute) as set by count logic 498. If, however, it is confirmed by count logic 498 that at least two notes have been confirmed within the filtered signal 500 (e.g., confirmed by note confirm logic 484) then a confirm signal is latched by latch logic 499 and cannot be reset. A true ALARM_DETECTED output 344 is provided upon confirmation that the alarm sound is present within the filtered signal 500. For example, as shown in FIG. 8A, upon satisfaction of the sound signature criteria (e.g., at least two notes identified), a false state 512 is changed to a true state 514 after the second note has been detected or confirmed indicative of a determination that the speaker was operable to broadcast the alarm sound and that the sound was audible to a user.

Each of the high priority alarm, medium priority alarm, and low priority alarm may be confirmed in the same manner as described above when commanded to be broadcast by the speaker (e.g., common predefined sound signature criteria are used; the criteria being common to all of these alarms). As such, this logic does not differentiate between the different alarms, but such differentiation could be provided with additional logic (e.g., based on one or more other sound signature criteria such as note spacing).

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed is:

1. A medical treatment device for use in providing a treatment to a patient, the medical treatment device comprising:
   a speaker operable to broadcast one or more types of sounds, wherein the one or more types of sounds comprise at least one of an alarm sound and a test sound, wherein the alarm sound comprises a plurality of spaced apart notes with each note having a duration, an amplitude, and a frequency, wherein each test sound comprises a note having a duration, an amplitude, and a frequency, wherein each type of sound is associated with a predefined sound signature, wherein the sound signature corresponding to an alarm sound comprises criteria based at least on the amplitude and duration of at least two notes of the plurality of spaced apart notes, and further wherein the sound signature corresponding to a test sound comprises criteria based on the amplitude and duration of the note thereof;
   an acoustic transducer to generate a sound signal representative of a sound when broadcast by the speaker; and
   processing circuitry configured to:
   command the speaker to broadcast a sound of the one or more types of sounds;
   monitor and store the sound signal generated by the acoustic transducer during a time period when the speaker is expected to broadcast the sound; and
   determine if the speaker was operable to broadcast the sound and whether the sound was audible to a user by comparing the stored sound signal to the sound signature associated with the type of sound commanded to be broadcast.

2. The device of claim 1, wherein the criteria of a sound signature corresponding to an alarm sound or a test sound are independent of frequency.

3. The device of claim 1,
   wherein the one or more types of sounds comprise a plurality of types of alarm sounds, wherein each type of alarm sound comprises a different plurality of spaced apart notes with each note having a duration, an amplitude, and a frequency, wherein the plurality of types of alarm sounds are associated with a common predefined sound signature, wherein the common predefined sound signature is based at least on the amplitude and duration of at least two notes of the plurality of spaced apart notes of each of the plurality of types of alarm sounds, wherein the processing circuitry is further configured to command the speaker to broadcast an alarm sound of the plurality of types of alarm sounds, and determine if the speaker was operable to broadcast the alarm sound and whether the alarm sound was audible to a user by comparing the stored sound signal to the common predefined sound signature associated with the plurality of types of alarm sounds.

4. The device of claim 1, wherein the one or more types of sounds comprise a plurality of types of alarm sounds, wherein each type of alarm sound comprises a different plurality of spaced apart notes with each note having a duration, an amplitude, and a frequency, wherein each of the plurality of types of alarm sounds are associated with a predefined sound signature, wherein the predefined sound signature is based at least on the amplitude and duration of at least two notes of the plurality of spaced apart notes of each of the plurality of types of alarm sounds and the spacing between the plurality of spaced apart notes, wherein the processing circuitry is further configured to command the speaker to broadcast an alarm sound of the plurality of types of alarm sounds, and determine if the speaker was operable to broadcast the alarm sound and whether the alarm sound was audible to a user by comparing the stored sound signal to the predefined sound signatures associated with the types of alarm sounds.

5. The device of claim 1, wherein the sound is a test sound, and wherein the processing circuitry is further configured to:

filter the sound signal generated by the acoustic transducer to provide a filtered sound signal; and compare the amplitude of the filtered sound signal to an amplitude threshold of the sound signature, wherein a test sound is detected if the amplitude of the filtered sound is greater than the amplitude threshold for a time exceeding a duration time threshold of the sound signature.

6. The device of claim 1, wherein the sound is an alarm sound, and wherein the processing circuitry is further configured to:

filter the sound signal generated by the acoustic transducer to provide a filtered sound signal;

compare the amplitude of the filtered sound signal to an amplitude threshold of the sound signature, wherein a note of the plurality of notes defining the alarm sound is detected if the amplitude of the filtered sound is greater than the amplitude threshold for a time exceeding a note duration time threshold of the sound signature; and determine the existence of a predetermined number of detected notes based on the sound signature, wherein an alarm sound is detected if the number of detected notes exceeds a predetermined number within an alarm duration time threshold of the sound signature.

7. The device of claim 6, wherein the processing circuitry is further configured to filter the sound signal generated by the acoustic transducer by applying an amplitude/difference filter to the sound signal and then smoothing the signal to provide the filtered sound signal.

8. The device of 7, wherein applying an amplitude/difference filter to the sound signal comprises taking a derivative of the sound signal.

9. The device of claim 1, wherein the processing circuitry is further configured to command the speaker to broadcast at least two different alarm sounds having different patterns of spaced apart notes, and further wherein it is determined whether the speaker was operable to broadcast each of the at least two different alarm sounds.

10. The device of claim 9, wherein the each alarm sound of the at least two different alarm sounds having different patterns of spaced apart notes comprises one or more notes having at least one of a different amplitude, a different duration, and a different frequency than at least one other note of a different alarm sound.

11. The device of claim 1, wherein the processing circuitry is further configured to:

command the speaker to broadcast a sound using a driver associated with control circuitry of the medical treatment device that controls treatment of a patient, and further wherein it is determined whether the speaker was operable to broadcast the sound; and command the speaker to broadcast a sound based using a driver associated with circuitry different than the control circuitry of the medical treatment device, and further wherein it is determined whether the speaker was operable to broadcast the sound.

12. The device of claim 1, wherein the processing circuitry is further configured to:

command a primary speaker to broadcast a sound, and further wherein it is determined whether the primary speaker was operable to broadcast the sound; and command a backup speaker to broadcast a sound, and further wherein it is determined whether the backup speaker was operable to broadcast the sound.

13. The device of claim 1, wherein the device comprises an extracorporeal blood treatment apparatus.

14. The device of claim 1, wherein the processing circuitry is further configured to alarm or allow the medical treatment device to be placed in a mode to provide treatment based on whether the speaker was operable to broadcast the sound and whether the sound was audible to a user.

15. A method for a medical treatment device, wherein the medical treatment device comprises a speaker operable to broadcast one or more types of sounds, wherein the one or more types of sounds comprise at least one of an alarm sound and a test sound, wherein each alarm sound comprises a plurality of spaced apart notes with each note having a duration, an amplitude, and a frequency, wherein each test sound comprises a note having a duration, an amplitude, and a frequency, wherein the method comprises:

commanding the speaker to produce a sound of the one or more types of sounds, wherein each type of sound is associated with a predefined sound signature, wherein the sound signature corresponding to an alarm sound comprises criteria based at least on the amplitude and duration of at least two notes of the plurality of spaced apart notes, and further wherein the sound signature corresponding to a test sound comprises criteria based on the amplitude and duration of the note thereof;

monitoring and storing a sound signal generated by an acoustic transducer during a time period when the speaker is expected to broadcast the sound; and determining if the speaker was operable to broadcast the sound and whether the sound was audible to a user by comparing the stored sound signal to the sound signature associated with the type of sound commanded to be broadcast.

16. A medical treatment device for use in providing a treatment to a patient, the medical treatment device comprising:
a speaker operable to broadcast one or more types of sounds, wherein the one or more types of sounds comprise at least one of an alarm sound and a test sound, wherein the alarm sound comprises a plurality of spaced apart notes with each note having a duration, an amplitude, and a frequency, wherein each test sound comprises a note having a duration, an amplitude, and a frequency, wherein each type of sound is associated with a predefined sound signature, wherein the sound signature corresponding to an alarm sound or a test sound is independent of frequency;
an acoustic transducer to generate a sound signal representative of a sound when broadcast by the speaker; and
processing circuitry configured to:
command the speaker to broadcast a sound of the one or more types of sounds;
monitor and store the sound signal generated by the acoustic transducer during a time period when the speaker is expected to broadcast the sound; and
determine if the speaker was operable to broadcast the sound and whether the sound was audible to a user by comparing the stored sound signal to the sound signature associated with the type of sound commanded to be broadcast.

17. A medical treatment device for use in providing a treatment to a patient, the medical treatment device comprising:
a speaker operable to broadcast one or more types of sounds, wherein the one or more types of sounds comprise a plurality of types of alarm sounds, wherein each type of alarm sound comprises a different plurality of spaced apart notes with each note having a duration, an amplitude, and a frequency, wherein the plurality of types of alarm sounds are associated with a common predefined sound signature, wherein the common predefined sound signature is based at least on the amplitude and duration of at least two notes of the plurality of spaced apart notes of each of the plurality of types of alarm sounds;
an acoustic transducer to generate a sound signal representative of a sound when broadcast by the speaker; and
processing circuitry configured to:
command the speaker to broadcast an alarm sound of the plurality of types of alarm sounds;
monitor and store the sound signal generated by the acoustic transducer during a time period when the speaker is expected to broadcast the alarm sound; and
determine if the speaker was operable to broadcast the alarm sound and whether the alarm sound was audible to a user by comparing the stored sound signal to the common predefined sound signature associated with the plurality of types of alarm sounds.

* * * * *